United States Patent
Lee et al.

(10) Patent No.: US 10,317,702 B2
(45) Date of Patent: Jun. 11, 2019

(54) FAILSAFE OPERATION OF EYE-MOUNTABLE DEVICE

(71) Applicant: VERILY LIFE SCIENCES LLC, Mountain View, CA (US)

(72) Inventors: Shungneng Lee, Sunnyvale, CA (US); Daniel James Yeager, Berkeley, CA (US); Jennifer Han, Palo Alto, CA (US); Nathan Pletcher, Mountain View, CA (US); Brian Otis, Saratoga, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 232 days.

(21) Appl. No.: 14/737,266

(22) Filed: Jun. 11, 2015

(65) Prior Publication Data

US 2015/0362755 A1    Dec. 17, 2015

Related U.S. Application Data

(60) Provisional application No. 62/012,005, filed on Jun. 13, 2014.

(51) Int. Cl.
     *G02C 7/08*           (2006.01)
     *G02C 7/04*           (2006.01)
     *A61B 5/00*           (2006.01)

(52) U.S. Cl.
     CPC ............ *G02C 7/083* (2013.01); *A61B 5/6821* (2013.01); *G02C 7/04* (2013.01); *A61B 2560/0204* (2013.01)

(58) Field of Classification Search
     CPC ........ G02C 7/083; G02C 7/04; A61B 5/6821; A61B 2560/0204
(Continued)

(56) References Cited

U.S. PATENT DOCUMENTS

| | | |
|---|---|---|
| 7,019,890 B2 | 3/2006 | Meredith et al. |
| 7,247,168 B2 | 7/2007 | Esch et al. |

(Continued)

FOREIGN PATENT DOCUMENTS

| | | |
|---|---|---|
| EP | 2 518 555 A1 | 10/2012 |
| JP | 2006317932 A | 11/2006 |

(Continued)

OTHER PUBLICATIONS

International Search Report and Written Opinion for PCT Application No. PCT/US2015/035663 dated Dec. 22, 2016, 13 pages.

(Continued)

*Primary Examiner* — Kristina M Deherrera
(74) *Attorney, Agent, or Firm* — Christensen O'Connor Johnson Kindness PLLC

(57) ABSTRACT

An embodiment of an eye-mountable device includes an optical lens; an accommodation actuator to provide vision accommodation for the optical lens; a controller including an accommodation logic to select one of a plurality of vision accommodation states for the device, the plurality of vision accommodation states including at least a failsafe focal distance; and a failsafe subsystem including a system health detector, the system health detector to monitor for one or more operational indicators for the device, wherein the failsafe subsystem is to cause the device to transition to a failsafe mode upon the failsafe subsystem identifying a failure condition for the device, the failsafe mode includes setting the vision accommodation state to be the failsafe focal distance.

13 Claims, 4 Drawing Sheets

(58) Field of Classification Search
USPC .............. 351/159.03, 159.39–159.4, 159.34
See application file for complete search history.

(56) References Cited

U.S. PATENT DOCUMENTS

| | | | |
|---|---|---|---|
| 7,311,398 | B2 | 12/2007 | Kuiper et al. |
| 7,728,949 | B2 | 6/2010 | Clarke et al. |
| 8,634,145 | B2 | 1/2014 | Pugh et al. |
| 8,636,358 | B2 | 1/2014 | Binder |
| 8,834,566 | B1 | 9/2014 | Jones |
| 9,241,669 | B2 | 1/2016 | Pugh et al. |
| 2005/0073739 | A1 | 4/2005 | Meredith et al. |
| 2007/0153405 | A1 | 7/2007 | Kuiper et al. |
| 2007/0216864 | A1 | 9/2007 | Blum et al. |
| 2007/0285759 | A1 | 12/2007 | Ash et al. |
| 2008/0180630 | A1 | 7/2008 | Clarke et al. |
| 2008/0208335 | A1 | 8/2008 | Blum et al. |
| 2009/0033866 | A1 | 2/2009 | Blum et al. |
| 2011/0228212 | A1 | 9/2011 | Blum et al. |
| 2012/0075712 | A1 | 3/2012 | Pugh et al. |
| 2012/0140167 | A1* | 6/2012 | Blum .................. A61F 2/1624 351/159.34 |
| 2012/0236417 | A1 | 9/2012 | Pugh et al. |
| 2012/0245444 | A1 | 9/2012 | Otis et al. |
| 2012/0268712 | A1 | 10/2012 | Egan et al. |
| 2013/0258275 | A1 | 10/2013 | Toner et al. |
| 2013/0258277 | A1 | 10/2013 | Pugh et al. |
| 2014/0022505 | A1 | 1/2014 | Pugh et al. |
| 2014/0107447 | A1 | 4/2014 | Liu et al. |
| 2014/0107448 | A1 | 4/2014 | Liu et al. |
| 2014/0156000 | A1 | 6/2014 | Campin et al. |
| 2014/0192318 | A1 | 7/2014 | Guth et al. |
| 2014/0194773 | A1 | 7/2014 | Pletcher et al. |
| 2014/0209481 | A1 | 7/2014 | Pletcher et al. |
| 2014/0213867 | A1 | 7/2014 | Pletcher et al. |
| 2014/0240655 | A1 | 8/2014 | Pugh et al. |
| 2014/0240665 | A1 | 8/2014 | Pugh et al. |
| 2014/0243971 | A1 | 8/2014 | Pugh et al. |
| 2014/0327875 | A1 | 11/2014 | Blum et al. |

FOREIGN PATENT DOCUMENTS

| | | | | |
|---|---|---|---|---|
| JP | 20100517082 | A | | 5/2010 |
| JP | 2014021500 | A | | 2/2014 |
| WO | 2012061411 | A1 | | 5/2012 |
| WO | 2013036789 | A1 | | 3/2013 |
| WO | WO 2013036789 | A1 | * | 3/2013 .............. C09K 9/02 |

OTHER PUBLICATIONS

PCT/US2015/035663—International Search Report and Written Opinion, dated Oct. 1, 2015, 21 pages.
De Smet, J. et al., "Progress toward a liquid crystal contact lens display", Journal of the SID 21/9, DOI: 10.1002/jsid.188, 2014 pp. 399-406.
De Smet, J. et al., "A Liquid Crystal Based Contact Lens Display Using PEDOT: PSS and Obliquely Evaporated SiO2", Late-News Poster, SID 2012 Digest, pp. 1375-1378.
Milton, H. et al., "Optimization of refractive liquid crystal lenses using an efficient multigrid simulation", May 2012, vol. 20, No. 10, Optics Express, pp. 11159-11165.
Milton, H. et al., "Switchable liquid crystal contact lenses: dynamic vision for the ageing eye", Proc. of SPIE vol. 9004 90040H, 6 pages. Downloaded From: http://spiedigitallibrary.org/ on Mar. 28, 2014.
Milton, H. et al., "Electronic liquid crystal contact lenses for the correction of presbyopia", Apr. 2014, vol. 22, No. 7, DOI:10.1364/OE.22.008035, Optics Express, pp. 8035-8040.
Tremblay, E. et al. "Switchable telescopic contact lens", Jul. 2013, vol. 21, No. 13, DOI:10.1364/OE.21.015980, Optics Express, pp. 15980-15986.
Extended European Search Report for EP Application 15806857.7, dated Nov. 29, 2017, 7 pages.
AU 2015275156—First Examination Report dated Sep. 11, 2017, 3 pages.
RU 2015275156—First Office Action dated Mar. 13, 2018, 14 pages.
Notice of Reason for Rejection issued in Japanese Patent Application No. 2016-567925, dated Dec. 27, 2017, 11 pages.
CN 201580031770.5—First Office Action dated Jul. 27, 2018, 20 pages.
JP 2016-567925—Notice of Reasons for Rejection dated Sep. 13, 2018, 7 pages.
First Examination Report for Indian Patent Application 201647040759, dated Jan. 17, 2019, 6 pages.
Second Office Action for Chinese Patent Application 201580031770.5, dated Mar. 14, 2019, 20 pages.

* cited by examiner

US 10,317,702 B2

FAILSAFE OPERATION OF EYE-MOUNTABLE DEVICE

CROSS REFERENCE TO RELATED APPLICATIONS

This application claims priority under the provisions of 35 U.S.C. § 119(e) to U.S. Provisional Application No. 62/012,005, filed on Jun. 13, 2014, entitled "Accommodating Lens", contents of which are hereby incorporated by reference.

TECHNICAL FIELD

This disclosure relates generally to the field of optics, and in particular but not exclusively, relates to eye-mountable devices including contact lenses.

BACKGROUND INFORMATION

Accommodation is a process by which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and applies a force on the elastic lens during muscle contractions that change the focal point of the elastic lens.

As an individual ages, the effectiveness of the ciliary muscle degrades. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to substantially rise as the world's population ages. Techniques and devices that can help individuals offset the effects of Presbyopia are increasingly in demand.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Figure 1:
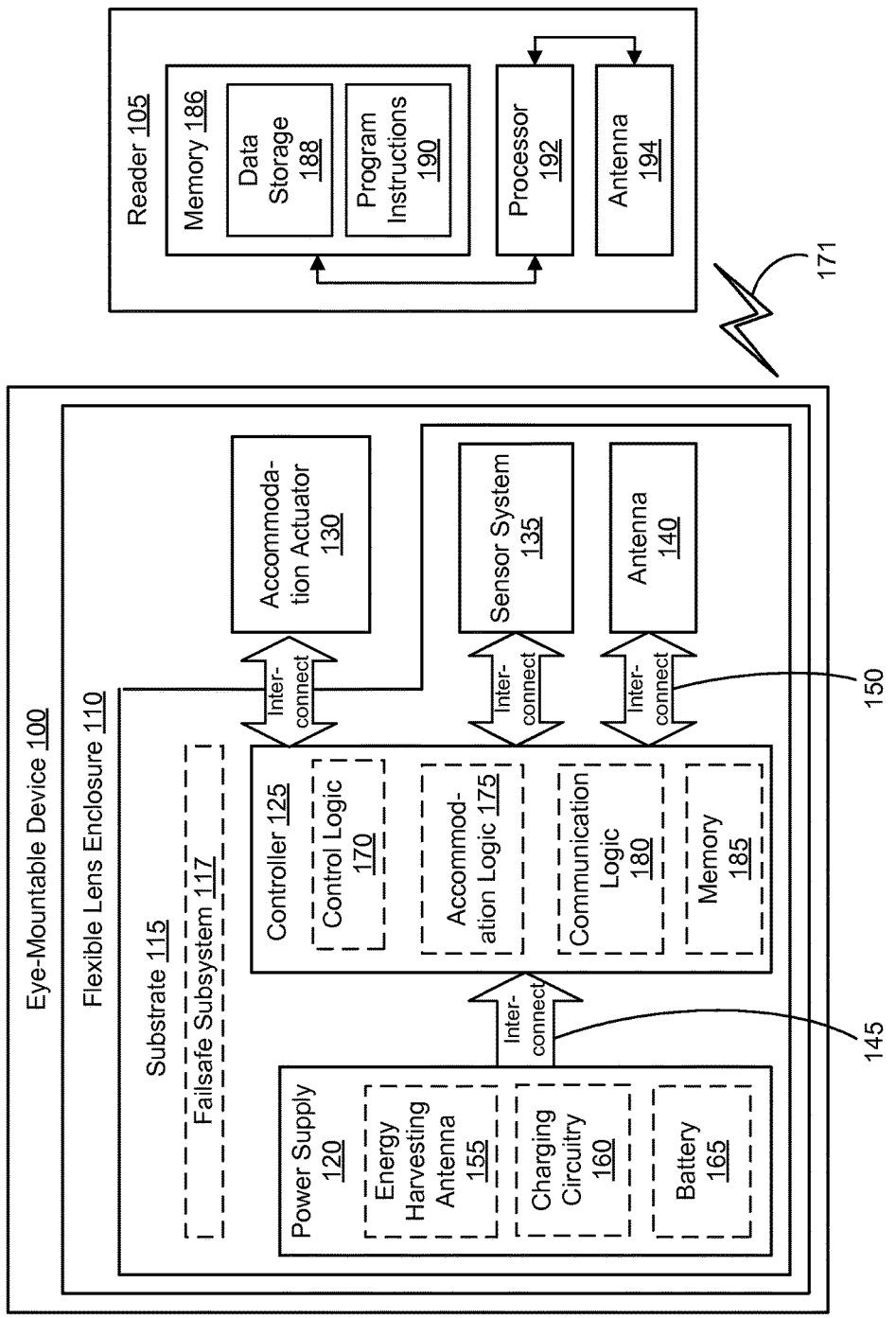
FIG. 1 is a functional block diagram of an eye-mountable device that provides auto-accommodation and an external reader for interacting with the eye-mountable device, in accordance with an embodiment.

Embodiments of a system, apparatus, and method for failsafe operation of eye-mountable devices are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In some embodiments, an eye-mountable device, which may include a smart contact lens or similar device, includes a failsafe subsystem and operation. Described herein is a smart contact lens or other eye-mountable device that includes an accommodation actuator for adjusting the focal distance of an optical lens of the device to one of multiple different vision accommodation states. The vision accommodation states may include, for example, a near field state and a far field state, but may include other states, such as a middle field state between the near field state and the far field state. In some embodiments, the vision accommodation is automatically adjusted in real-time based upon a user's gazing direction. The accommodation actuator is disposed in a center region of the smart contact lens (e.g., covering at least the foveal vision).

However, an eye-mountable device will have accommodation states that may not be appropriate in all circumstances. In an example, a near field accommodation state to provide vision accommodation for vision of objects at close distances may provide a danger if the lens or device remains in near field accommodation in a failure condition. For example, an incorrect accommodation state may create a danger in operation such as driving a motor vehicle, riding a bicycle, or otherwise piloting or riding a moving vehicle, or any other activity in which distance vision is needed immediately for safety.

In some embodiments, a failsafe mode for an eye-mountable device transitions the eye-mountable device to a failsafe focal distance. In some embodiments, the failsafe focal distance is a far field (distance vision) accommodation state because the far field vision setting generally allows a user to safely handle any situation, including operations in which a failure to any other vision setting may be life threatening. However, the specific failsafe focal distance may vary in different implementations. In some embodiments, an eye-mountable device is to fail into the failsafe focal distance to provide for safe operation in any failure condition. As used herein, a failure condition includes any device failure, shutdown condition, power loss, or other condition in which one or more functions of the eye-mountable device, such as the auto-accommodation function, are not operating properly.

In some embodiments, a failsafe subsystem of an eye-mountable device is to monitor indicators for failure conditions and to provide that the optics of the device enter into a failsafe focal distance upon the detection of a failure condition. In some embodiments, the failsafe subsystem includes one or more of:

(1) System health detection, including monitoring of one or more operational indicators for the device, the one or more operational indicators including one or more of sensor values, vision accommodation states, health of the accommodation actuator, and electrical and power issues.

(2) Timeout condition monitoring.

(3) Response to failsafe commands.

(4) Initializing to a state including a failsafe focal distance on initialization or reset.

(5) Failsafe focal distance default features.

In some embodiments, an eye-mountable device is to remain in the failsafe mode until one or more conditions are met for leaving the failsafe mode. In some embodiments, such conditions may include one or more of receiving a positive command for leaving the failsafe mode; waiting for a certain period of time to expire; and successfully completing a health check of the device.

Embodiments of the eye-mountable device may include a power supply, control electronics, an accommodation actuator, a gaze direction sensor system, and an antenna all embedded within a flexible lens enclosure formed to be contact mounted to an eye (e.g., shaped to be removeably mounted to a cornea and allow eyelid motion to open and close). In one embodiment, the control electronics are coupled to monitor the sensor system to identify gaze direction/focal distance, manipulate the accommodation actuator to control the optical power of the eye-mountable device, and provide wireless communications with an external reader. In some embodiments, the power supply may include charging circuitry for controlling inductive wireless charging of an embedded battery.

The flexible lens enclosure may be fabricated of a variety of materials compatible for direct contact with a human eye, such as a polymeric material, a hydrogel, PMMA (polymethyl methacrylate), silicone based polymers (e.g., fluoro-silicone acrylate), or otherwise. The electronics may be disposed upon a ring substrate embedded within the flexible lens enclosure near its periphery to avoid interference with incident light received closer to the central region of the cornea. The sensor system may be arranged on the substrate to face outward towards the eyelids to detect the gaze direction/focal distance based upon the amount and position of eyelid coverage over the sensor system. As the eyelids cover different portions of the sensor system, this changes a characteristic (e.g., its capacitance), which can be measured to determine gaze direction and/or focal distance.

In some embodiments, the gaze direction/focal distance information can then be used to determine the amount of accommodation to be applied via a see-through accommodation actuator positioned in a central portion of the flexible lens enclosure. The accommodation actuator is coupled to the controller to be electrically manipulated thereby via the application of a voltage across a pair of flexible conductive electrodes. For example, the accommodation actuator may be implemented with a liquid crystal cell that changes its index of refraction in response to an applied electrical bias signal across the flexible conductive electrodes. In other embodiments, the accommodation actuator may be implemented using other types of electro-active materials such as electro-optic materials that vary refractive index in the presence of an applied electric field or electro-mechanical structures that change the shape of a deformable lens. Other example structures that may be used to implement the accommodation actuator include electrowetting optics, micro-electro-mechanical systems, or otherwise.

In some embodiments, a device includes means for providing vision accommodation for an optical lens, including means for selecting one of a plurality of vision accommodation states for the device; means for monitoring one or more operational indicators for the device; and means for transitioning the device to a failsafe mode upon detecting a failure condition for the device, the failsafe mode including establishing a failsafe focal distance for the vision accommodation state. In some embodiments, the failsafe focal distance is a far field state.

In some embodiments, the means for monitoring of one or more operational indicators includes means for monitoring sensor values, and the device further includes means for detecting a failure condition if one or more sensor values are outside of a good range for the sensor.

In some embodiments, the means for monitoring of one or more operational indicators includes means for monitoring vision accommodation results for the device, and the device further includes means for detecting a failure condition if vision accommodation results are incorrect.

In some embodiments, the means for monitoring of one or more operational indicators includes means for monitoring for electrical or power issues, wherein a failure condition is detected if one or more electrical or power properties for the device are outside of good ranges.

In some embodiments, the device further includes means for monitoring for occurrence of timeout conditions for the device, and means to transition the device to the failsafe mode upon determining that a timeout condition has occurred.

In some embodiments, the device further includes means for monitoring for receipt of failsafe commands, and means for transitioning the device to the failsafe mode upon receiving a failsafe command.

In some embodiments, the device includes means for initializing or resetting the device; means for setting the vision accommodation state to the failsafe focal distance; means for performing a health check for the device; and means for proceeding to the vision accommodation for the optical lens upon successfully completing the health check. In some embodiments, a default state for the optical lens is the failsafe focal distance, the device including means to transition the optical lens to the failsafe focal distance upon a power loss for the device.

In some embodiments, the device includes means for overriding the accommodation logic in the failsafe mode.

FIG. 1 is a functional block diagram of an eye-mountable device 100 with gaze tracking for auto-accommodation along with an external reader 105, in accordance with an embodiment of the disclosure. The exposed portion of eye-mountable device 100 is a flexible lens enclosure 110 formed to be contact-mounted to a corneal surface of an eye. A substrate 115 is embedded within or surrounded by flexible lens enclosure 110 to provide a mounting surface for a power supply 120, a controller 125, a sensor system 135, an antenna 140, and various interconnects 145 and 150. An accommodation actuator 130 is embedded within flexible lens enclosure 110 and coupled to controller 125 to provide auto-accommodation to the wearer of eye-mountable device 100. The illustrated embodiment of power supply 120 includes an energy harvesting antenna 155, charging circuitry 160, and a battery 165. The illustrated embodiment of controller 125 includes control logic 170, accommodation logic 175, communication logic 180, and a memory for storage of data and instructions 185. The illustrated embodiment of reader 105 includes a processor 192, an antenna 194, and memory 186, wherein the memory may include data storage 188 and program instructions 190.

In some embodiments, the device further includes a failsafe subsystem 117, wherein the failsafe subsystem 117 is to monitor operational indicators for the device, and is to transition the eye-mountable device 100 to a failsafe mode upon detection of a failure condition for the device 100. In some embodiments, the failsafe subsystem 117 is operable to override the accommodation logic 175 upon detecting a failure condition. While the failsafe subsystem 117 is illustrated as being separate from other elements of the device 100 for ease of illustration, in some embodiments portions of the failsafe subsystem are incorporated into other elements of the device 100.

Controller 125 is coupled to receive feedback control signals from sensor system 135 and further coupled to operate the accommodation actuator 130. Power supply 120 supplies operating voltages to the controller 125 and/or the accommodation actuator 130. Antenna 140 is operated by the controller 125 to communicate information to and/or from eye-mountable device 100. In one embodiment, antenna 140, controller 125, power supply 120, at least a portion of failsafe subsystem 117, and sensor system 135 are all situated on the embedded substrate 115. In one embodiment, accommodation actuator 130 is embedded within a center region of flexible lens enclosure 110, but is not disposed on substrate 115. Because eye-mountable device 100 includes electronics and is configured to be contact-mounted to an eye, it is also referred to herein as an ophthalmic electronics platform, a contact lens, or a smart contact lens.

To facilitate contact-mounting, the flexible lens enclosure 110 can have a concave surface configured to adhere ("mount") to a moistened corneal surface (e.g., by capillary forces with a tear film coating the corneal surface). Additionally or alternatively, the eye-mountable device 100 can be adhered by a vacuum force between the corneal surface and flexible lens enclosure 110 due to the concave curvature. While mounted with the concave surface against the eye, the outward-facing surface of flexible lens enclosure 110 can have a convex curvature that is formed to not interfere with eyelid motion while the eye-mountable device 100 is mounted to the eye. For example, flexible lens enclosure 110 can be a substantially transparent curved disk shaped similarly to a contact lens.

Flexible lens enclosure 110 can include one or more biocompatible materials, such as those employed for use in contact lenses or other ophthalmic applications involving direct contact with the corneal surface. Flexible lens enclosure 110 can optionally be formed in part from such biocompatible materials or can include an outer coating with such biocompatible materials. Flexible lens enclosure 110 can include materials configured to moisturize the corneal surface, such as hydrogels and the like. Flexible lens enclosure 110 is a deformable ("non-rigid") material to enhance wearer comfort. In some instances, flexible lens enclosure 110 can be shaped to provide a predetermined, vision-correcting optical power, such as can be provided by a contact lens. Flexible lens enclosure 110 may be fabricated of various materials including a polymeric material, a hydrogel, PMMA, silicone based polymers (e.g., fluoro-silicon acrylate), or otherwise.

Substrate 115 includes one or more surfaces suitable for mounting sensor system 135, controller 125, power supply 120, failsafe subsystem 117, and antenna 140. Substrate 115 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or the flexible conductive materials discussed below) can be patterned on substrate 115 to form circuitry, electrodes, etc. For example, antenna 140 can be formed by depositing a pattern of gold or another conductive material on substrate 115. Similarly, interconnects 145 and 150 can be formed by depositing suitable patterns of conductive materials on substrate 115. A combination of resists, masks, and deposition techniques can be employed to pattern materials on substrate 115. Substrate 115 can be a relatively rigid material, such as polyethylene terephthalate ("PET") or another material sufficient to structurally support the circuitry and/or electronics within enclosure material 110. Eye-mountable device 100 can alternatively be arranged with a group of unconnected substrates rather than a single substrate. For example, controller 125 and power supply 120 can be mounted to one substrate, while antenna 140 and sensor system 135 are mounted to another substrate and the two can be electrically connected via interconnects.

Substrate 115 can be shaped as a flattened ring with a radial width dimension sufficient to provide a mounting platform for the embedded electronics components. Substrate 115 can have a thickness sufficiently small to allow the substrate to be embedded in flexible lens enclosure 110 without adversely influencing the profile of eye-mountable device 100. Substrate 115 can have a thickness sufficiently large to provide structural stability suitable for supporting the electronics mounted thereon. For example, substrate 115 can be shaped as a ring with a diameter of about 10 millimeters, a radial width of about 1 millimeter (e.g., an outer radius 1 millimeter larger than an inner radius), and a thickness of about 50 micrometers. Substrate 115 can optionally be aligned with the curvature of the eye-mounting surface of eye-mountable device 100 (e.g., convex surface). For example, substrate 115 can be shaped along the surface of an imaginary cone between two circular segments that define an inner radius and an outer radius. In such an example, the surface of substrate 115 along the surface of the imaginary cone defines an inclined surface that is approximately aligned with the curvature of the eye mounting surface at that radius.

In some embodiments, power supply 120 and controller 125 (and the substrate 115) can be positioned away from the center of eye-mountable device 100 and thereby avoid interference with light transmission to the eye through the center of eye-mountable device 110. In contrast, accommodation actuator 130 can be centrally positioned to apply optical accommodation to the light transmitted to the eye through the center of eye-mountable device 110. For example, where eye-mountable device 100 is shaped as a concave-curved disk, substrate 115 can be embedded around the periphery (e.g., near the outer circumference) of the disk. In some embodiments, sensor system 135 includes one or more discrete capacitance sensors that are peripherally distributed to sense the eyelid overlap.

In the illustrated embodiment, power supply 120 includes a battery 165 to power the various embedded electronics, including controller 125. Battery 165 may be inductively charged by charging circuitry 160 and energy harvesting antenna 155. In one embodiment, antenna 140 and energy harvesting antenna 155 are independent antennae, which serve their respective functions of energy harvesting and communications. In another embodiment, energy harvesting antenna 155 and antenna 140 are the same physical antenna that are time shared for their respective functions of inductive charging and wireless communications with reader 105. Charging circuitry 160 may include a rectifier/regulator to condition the captured energy for charging battery 165 or directly power controller 125 without battery 165. Charging circuitry 160 may also include one or more energy storage devices to mitigate high frequency variations in energy harvesting antenna 155. For example, one or more energy storage devices (e.g., a capacitor, an inductor, etc.) can be connected to function as a low-pass filter.

Controller 125 contains logic to choreograph the operation of the other embedded components. Control logic 170 controls the general operation of eye-mountable device 100, including providing a logical user interface, power control functionality, etc. Accommodation logic 175 includes logic for monitoring feedback signals from sensor system 135, determining the current gaze direction or focal distance of the user, and manipulating accommodation actuator 130 in response to provide the appropriate accommodation. The auto-accommodation can be implemented in real-time based upon feedback from the gaze tracking, or permit user control to select specific accommodation regimes (e.g., near field accommodation for reading, far field accommodation for regular activities, etc.). Communication logic 180 provides communication protocols for wireless communication with reader 105 via antenna 140. In one embodiment, communication logic 180 provides backscatter communication via antenna 140 when in the presence of an electromagnetic field 171 output from reader 105. In one embodiment, communication logic 180 operates as a smart wireless radio-frequency identification ("RFID") tag that modulates the impedance of antenna 140 for backscatter wireless communications. The various logic modules of controller 125 may be implemented in software/firmware executed on a general purpose microprocessor, in hardware (e.g., application specific integrated circuit), or a combination of both.

Eye-mountable device 100 may include various other embedded electronics and logic modules. For example, a light source or pixel array may be included to provide visible feedback to the user. An accelerometer or gyroscope may be included to provide positional, rotational, directional or acceleration feedback information to controller 125.

In some embodiments, an eye-mountable device includes a failsafe logic or subsystem, such as failsafe subsystem 117 illustrated in FIG. 1, to cause the device to switch to a failsafe focal distance. In some embodiments, the failsafe logic or subsystem includes one or more of the following:

(1) Operational Indicators for System Health—In some embodiments, an eye-mountable device is operable to monitor multiple operational indicators for the device, and to switch the device to a failsafe mode including a failsafe focal distance upon the detection of a failure condition. The failsafe focal distance may be, but is not limited to, a far field focal distance. In some embodiments, the device includes a system health detector to monitor the device operation indicators. In some embodiments, one or more detection circuits for monitoring of the device are powered using the same supply as the supply driving the optics.

As used herein, operational indicators to be monitored for an eye-mountable device may include but are not limited to:

(a) Sensor Values—In some embodiments, a system health detector is to monitor values for multiple sensors and other elements of an eye-mountable device, and is determine whether any of such values are outside of a good range. As used herein, a good range is a range of values that represent a normal or acceptable condition or operation. Stated in another way, operating in a good range may mean that the respective value or values generally are above or below a certain threshold, are between certain thresholds (such as above a first threshold and below a second threshold), or are otherwise within a certain set of values. Further, operating in a good range may include allowance of certain temporary transient values that are outside of a normal range for short periods of time.

In some embodiments, sensors monitored by the system health detector may include, but are not limited to: Accommodation actuator operation sensor; capacitive sensor or impedance sensor for optics; photodiode (PD) light sensor; conductivity sensor; temperature sensor; strain sensor; inertial sensor (accelerometer, magnetometer, gyroscope); and voltage or current detector.

In some embodiments, the system health detector may further monitor for sensor values with transient value issues, such as if certain transient properties vary too quickly or uncharacteristically over time, such as a collection of values that represent a signal trend that is uncharacteristic of a device or sensor that is operating normally. The determination regarding transient properties may include, but are not limited to, use of FIR (Finite Impulse Response), IIR (Infinite Impulse, Response), or other memory-based filter; a non-linear filter; or statistical analysis or other algorithms.

(b) Vision Accommodation States—In some embodiments, the system health detector is to monitor vision accommodation, and detect the production of incorrect accommodation values by algorithms or operations. Incorrect accommodation values may include accommodation values that fluctuate or vary rapidly, or that should not be produced in normal operating conditions. Among other potential problems, incorrect accommodation values may be produced if the calibration of the eye-mountable device is incorrect, such as in circumstances in which settings for the device are corrupted.

(c) Electrical and Power Issues—In some embodiments, the system health detector is to detect electrical and power issues. In some embodiments, issues include power loss such as a battery issue, high power usage that may require a shutdown, voltages or currents outside of good ranges, and other electrical and power conditions.

In some embodiments, detection of electrical and power issues includes detection of issues regarding transient electrical properties. If the transient electrical properties of the accommodating optic over time move strangely, this may indicate degradation of the optic, and thus should result into a failsafe failure into a failsafe focal distance, such a far field setting. The determination regarding transient properties may include, but are not limited to, use of FIR, IIR, or other memory-based filter; a non-linear filter; or statistical analysis or other algorithms.

In some embodiments, a device includes a brownout recovery flag. In some embodiments, if the chip browns out with low power conditions, and then recovers, the device can set a flag to be sent to logic that runs off of the battery to signal when chip is "healthy and ready to work"

(2) Timeout Condition—In some embodiments, the failsafe logic or subsystem may monitor for one or more timeout conditions that are indicative of a system issue. In one example, the system health detector may sense that a user hasn't blinked in a certain amount of time, which may indicate a sensor failure or, if any of the multi-bit or analog inputs of the system health monitor from the plurality of sensors that feed it stay at the same value for too long of a period of time, which behavior may signify a failure in certain circumstances.

(3) Failsafe Command—In some embodiments, the failsafe subsystem further includes one or more failsafe commands to direct the eye-mountable device to switch directly to the failsafe mode, thereby switching to a failsafe focal distance operation and ignoring algorithm determinations. In some embodiments, a process is provided overriding the current accommodation mode, which may be an automatic accommodation mode, a locked accommodation mode providing near field or far field accommodation, and moving to the failsafe mode. In some embodiments, a failsafe command allows a user, who may determine that the eye-mountable device is potentially operating improperly, to switch from the current accommodation mode to the failsafe mode by providing a manual override command.

In some embodiments, a failsafe command may include but is not limited to:

(a) A user input command from a user in operation of the eye-mountable device, such as, for example, a user blink pattern including, for example, blinking a certain number of times in a certain amount of time. In some embodiments, a blink pattern may detected by one or more sensors, such as, but not limited to, capacitive sensor, photodiode (PD) light sensor, strain sensor, pressure sensor, conductivity sensor, or temperature sensor. In some embodiments, a, eye-mountable device includes separate, blink-detector circuitry to allow operation when other circuitry fails, and may include a separate power connection to, for example, to run off of the battery directly.

Similarly, a user input may include other contact, such as a signal on a pressure or strain sensor or similar mechanism made by tapping on the eye (or on a closed eyelid) to engage the pressure or strain sensor.

(b) A radio signal from an external device, such as a reader device, to communicate with the eye-mountable device, wherein the external device may include a handheld device, smart phone, head/environmentally-mounted radio communicators, or other device.

(c) A visible or non-visible (such as infrared) light signal directed to the eye-mountable device.

(4) Setting to Failsafe Focal Distance on Initialization or Reset—In some embodiments, the eye-mountable device includes logic to lock the accommodation into an initial default failsafe focal distance upon initialization or reset of the device, wherein the logic does not release the setting lock until the device completes a health check. In this manner, the device is to start in the default failsafe focal distance upon initializing or resetting the eye-mountable device, including a re-start of the eye-mountable device.

(5) Failsafe Focal Distance Default Features—In some embodiments, an eye-mountable device includes one or more features for ensuring that the optics of the eye-mountable device reverts to failsafe focal distance for all powered optics (liquid crystal diffractive optic, electrowetting optic, MEMS/physical actuator-based optic, or other optics) when no power or voltage is applied to such optics. Stated in another way, the optics are configured such that the resting state of the optics without stimulation is a failsafe focal distance, such as a far field state. In this matter, if there is a power loss such that no power or voltage is applied to the optics, the optics will automatically rest at failsafe focal distance vision.

In a particular example, a liquid crystal cell may be configured to be in the failsafe focal distance state when no actuation is applied to it. Thus, if the battery runs out or there is otherwise a power failure, the optical accommodation enters the failsafe mode, wherein the optical accommodation is set to the failsafe focal distance.

In certain implementations, an optic may be bi-stable (or more generally multi-stable), indicating that the optics are stable in two (or more) states, and will remain in the current state if no stimulus is applied to the optic. In some embodiments, a lens includes a back-up stimulus to enable the return of the optic to a failsafe focal distance state upon the loss of power. In some embodiments, the back-up stimulus may include a charge from a capacitor that is applied to the optic in circumstances in which the lens is in a near field state (or other non-failsafe state) and there is a power loss.

In some embodiments, an eye-mountable device is to fail in a failsafe mode that includes a command to lock in the failsafe focal distance. In this manner, upon the eye-mountable device returning to operation, the device is set to remain in the failsafe focal distance state.

In some embodiments, an eye-mountable device includes an initial default setting, the device to start in the default setting upon initializing the eye-mountable device. In some embodiments, the initial default setting is to lock the eye-mountable device into the same setting as the failsafe mode, such setting being the failsafe focal distance. In this manner, in addition to the operation of the eye-mountable device on a failure condition, the initial default setting insures that the device remains in the failsafe mode on a re-start of the eye-mountable device.

Figure 2:
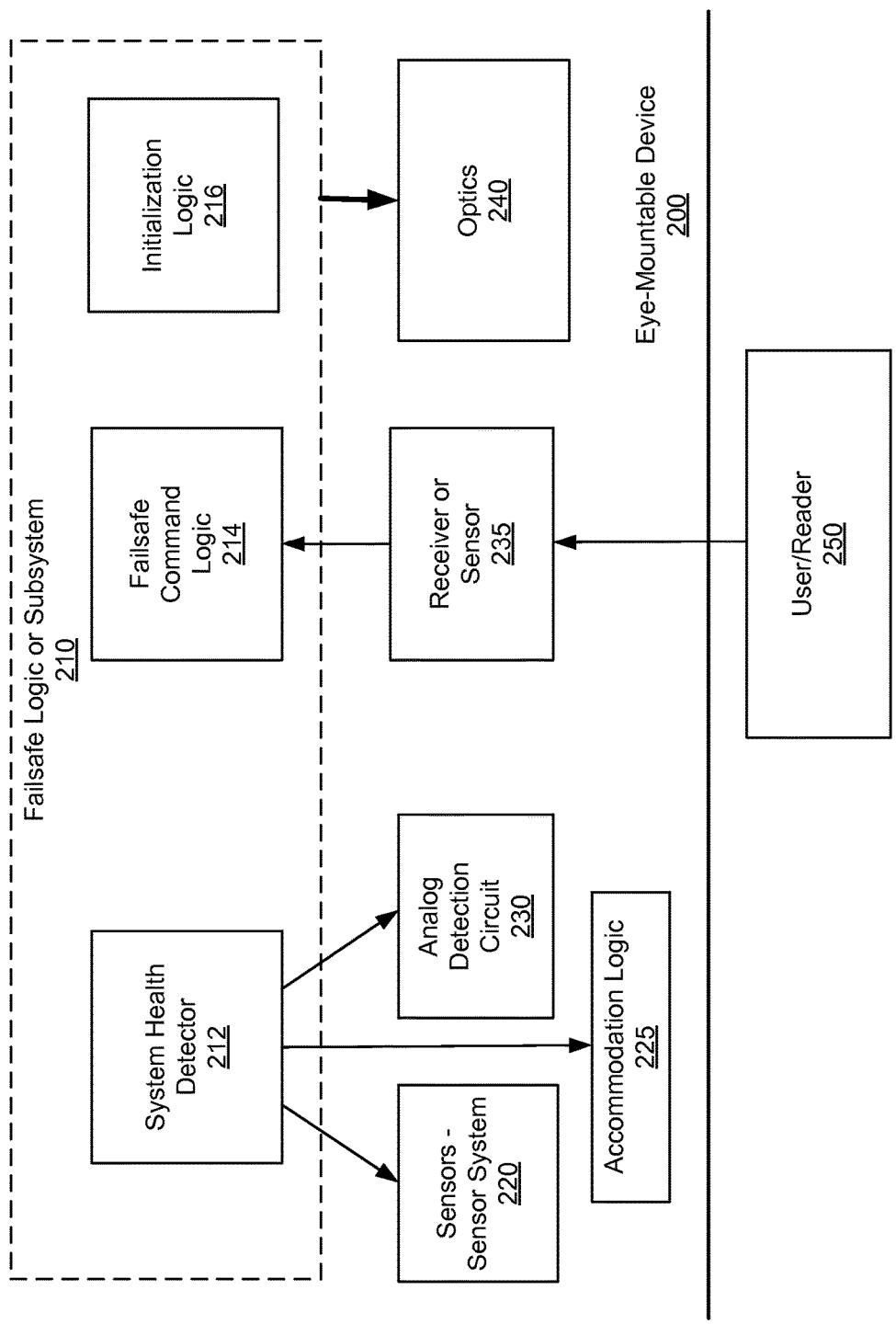
FIG. 2 is a block diagram to illustrate an eye-mountable device including a failsafe logic or subsystem according to an embodiment.

FIG. 2 is a block diagram to illustrate an eye-mountable device including a failsafe logic or subsystem according to an embodiment. FIG. 2 is intended to illustrate particular aspects of an eye-mountable device 200 in connection with failsafe operation, and such figure does not include all elements of the device 200.

In some embodiments, the eye-mountable device 200 includes a failsafe logic or subsystem 210, which may be the failsafe subsystem 117 illustrated in FIG. 1. While the elements of the failsafe logic 210 are illustrated together for purpose of illustration in FIG. 2, such elements are not necessarily located in a same location within the device and may not be physically or electrically connected.

In some embodiments, the failsafe logic 210 includes a system health detector to monitor operational indicators for the device 200, which may include monitoring multiple sensors 220, monitoring operation of accommodation logic 225, and monitoring various electrical and power values, which may include monitoring an analog detection circuit 230. In some embodiments, the analog detection circuit 230 may trip when supply voltages fall below some threshold (signifying brownout of chip).

In some embodiments, the failsafe logic 210 includes a failsafe command logic 214 to receive commands via a receiver or sensor 235 to transfer the device 200 into a failsafe mode. In some embodiments, the failsafe command logic may be separate from any normal command logic for the device. In some embodiments, a command from a user (such as a manual command) or from a reader (such as a wireless command), wherein the reader may be reader 105 illustrated in FIG. 1.

In some embodiments, the failsafe logic include an initialization logic 216 that causes accommodation for optics 240 to be locked into the failsafe focal distance setting (which may be, but is not limited to, a far field state) upon any initialization or reset of the device 200, and to hold the accommodation in the locked state until a health check for the device is successfully passed.

Figure 3:
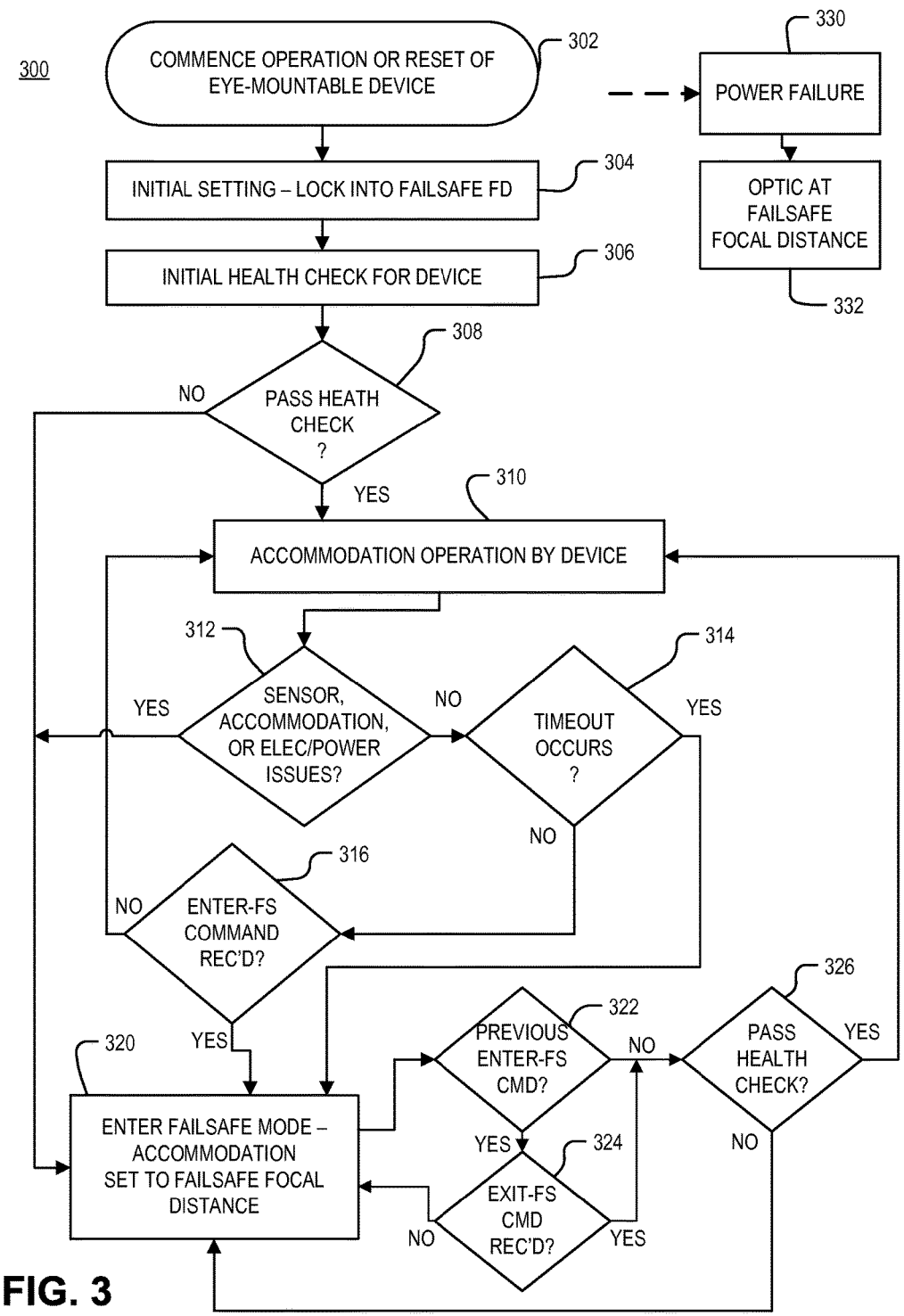
FIG. 3 is a flowchart to illustrate a failsafe process for an eye-mountable device according to an embodiment.

FIG. 3 is a flowchart to illustrate a failsafe process for an eye-mountable device according to an embodiment. In some embodiments, a failsafe process 300 includes, upon commencing operation or resetting the eye-mountable device 302, entering an initial setting including locking the optics of the device into a failsafe focal distance 304. An initial health check is then performed for the eye-mountable device 306.

In some embodiments, upon a failure of the initial health check 308 the eye-mountable device is to enter a failsafe mode, wherein the accommodation for the device optics is set to a failsafe focal distance state 320. In some embodiments, the failsafe focal distance is a far field setting. In some embodiments, upon passing the initial health check 308, the device enters accommodation operation 310, wherein the optics of the device are automatically modified based on current conditions, as described with regard to FIG. 1.

In some embodiments, upon entering the accommodation operation 310, the device is subject to one or more failsafe operations. Such operations may operate simultaneously or in any order. In some embodiments, the device may enter the failsafe mode 320 upon one or more of the following occurring:

(1) One or more sensor value, accommodation result, or electrical or power issues being detected 312.

(2) A timeout condition, which may indicate potential operation problems 314.

(3) Receipt of enter-failsafe command (enter-FS) from a user or from a reader device that is communicating with the eye-mountable device 316.

In some embodiments, if operation of the device is recoverable, the device is to remain in the failsafe mode 320, until, for example, receiving a command to exit the failsafe mode (exit-FS) 324 (if the failsafe mode was entered based on a previous enter-failsafe command 322) and passing a health check 326, wherein the process may then return to the accommodation mode 310. In some embodiments, the process may alternatively remain in the failsafe mode 320 until the device is reset or shut down, and can continue with the commence operation or reset process 302.

Further, at any point in operation, upon a power failure 330, such as a complete loss of power for the device, the optics of the device then enter a default, no power state, wherein the default state for the optics is a failsafe focal distance setting 332.

Figure 4A:
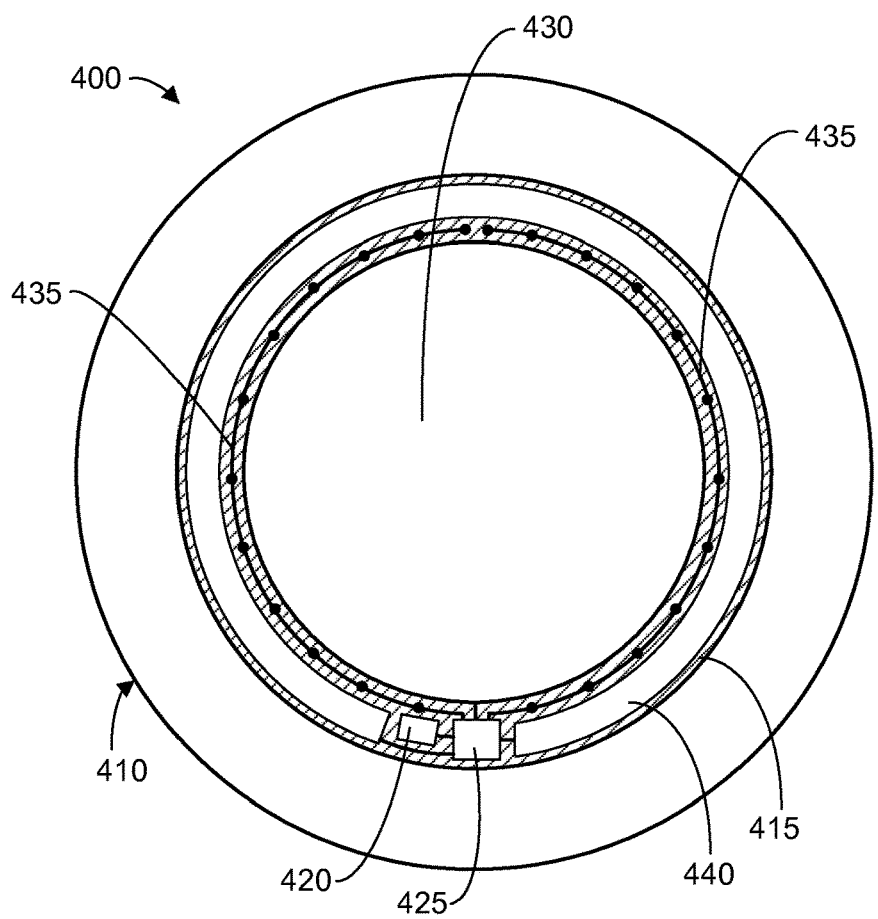
FIG. 4A is a top view illustration of an eye-mountable device, in accordance with an embodiment.
Figure 4B:
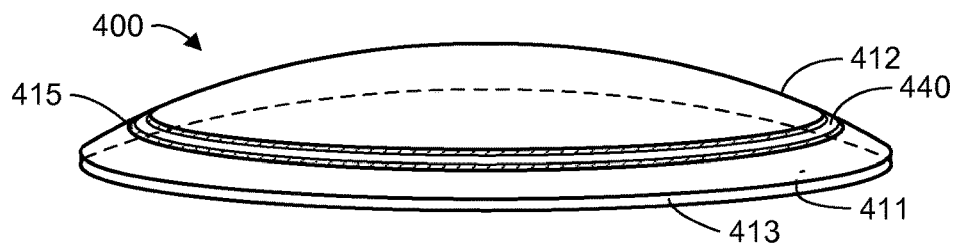
FIG. 4B is a perspective view illustration of an eye-mountable device, in accordance with an embodiment.

FIG. 4A and FIG. 4B illustrate two views of an eye-mountable device 400, in accordance with an embodiment of the disclosure. FIG. 4A is a top view of eye-mountable device 400 while FIG. 4B is a perspective view of the same. Eye-mountable device 400 is one possible implementation of eye-mountable device 100 illustrated in FIG. 1. In some embodiments, the eye-mountable device 400 includes a failsafe logic or subsystem such as illustrated as failsafe subsystem 117 in FIG. 1 or failsafe logic or subsystem 210 in FIG. 2.

The illustrated embodiment of eye-mountable device 400 includes a flexible lens enclosure 410, a ring substrate 415, a power supply 420, a controller 425, an accommodation actuator 430, a capacitive sensor system 435, and an antenna 440. It should be appreciated that FIGS. 4A and 4B are not necessarily drawn to scale, but have been illustrated for purposes of explanation only in describing the arrangement of the example eye-mountable device 400.

Flexible lens enclosure 410 of eye-mountable device 400 is shaped as a curved disk. Flexible lens enclosure 410 is formed with one side having a concave surface 411 suitable to fit over a corneal surface of an eye. The opposite side of the disk has a convex surface 412 that does not interfere with eyelid motion while eye-mountable device 400 is mounted to the eye. In the illustrated embodiment, a circular or oval outer side edge 413 connects the concave surface 411 and convex surface 412.

Eye-mountable device 400 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of eye-mountable device 400 can be selected according to the size and/or shape of the corneal surface of the wearer's eye. Flexible lens enclosure 410 can be formed with a curved shape in a variety of ways. For example, techniques similar to those employed to form vision-correction contact lenses, such as heat molding, injection molding, spin casting, etc. can be employed to form flexible lens enclosure 410.

Ring substrate 415 is embedded within flexible lens enclosure 410. Ring substrate 415 can be embedded to be situated along the outer periphery of flexible lens enclosure 410, away from the central region where accommodation actuator 430 is positioned. In the illustrated embodiment, ring substrate 415 encircles accommodation actuator 430. Ring substrate 415 does not interfere with vision because it is too close to the eye to be in focus and is positioned away from the central region where incident light is transmitted to the light-sensing portions of the eye. In some embodiments, ring substrate 415 can optionally be formed of a transparent material to further mitigate effects on visual perception. Ring substrate 415 can be shaped as a flat, circular ring (e.g., a disk with a centered hole). The flat surface of ring substrate 415 (e.g., along the radial width) is a platform for mounting electronics and for patterning conductive materials to form electrodes, antenna(e), and/or interconnections.

Capacitive sensor system 435 is distributed about eye-mountable device 400 to sense eyelid overlap in a manner similar to capacitive touch screens. By monitoring the amount and position of eyelid overlap, feedback signals from capacitive sensor system 435 can be measured by controller 425 to determine the approximate gaze direction and/or focal distance. In the illustrated embodiment, capacitive sensor system 435 is formed by a series of parallel coupled discrete capacitive elements. Other implementations may be used.

Accommodation actuator 430 is centrally positioned within flexible lens enclosure 410 to affect the optical power of eye-mountable device 400 in the user's center of vision. In various embodiments, accommodation actuator 430 includes an element that changes its index of refraction under the influence of flexible conductive electrodes manipulated by controller 425. By changing its refractive index, the net optical power of the curved surfaces of eye-mountable device 400 is altered, thereby applying controllable accommodation. Accommodation actuator 430 may be implemented using a variety of different optoelectronic elements. For example, accommodation actuator 430 may be implemented using a layer of liquid crystal (e.g., a liquid crystal cell) disposed in the center of flexible lens enclosure 410. In other embodiments, accommodation actuator 430 may be implemented using other types of electro-active optical materials such as electro-optic materials that vary the refractive index in the presence of an applied electric field. Accommodation actuator 430 may be a distinct device embedded within enclosure material 410 (e.g., liquid crystal cell), or a bulk material having a controllable refractive index. In yet another embodiment, accommodation actuator 430 may be implemented using a deformable lens structure that changes shape under the influence of an electrical signal. Accordingly, the optical power of eye-mountable device 400 is controlled by controller 425 with the application of electric signals via one or more electrodes extending from controller 425 to accommodation actuator 430.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An eye-mountable device, comprising:
   an optical lens;
   an accommodation actuator configurable to provide a plurality of vision accommodation states for vision accommodation by adjusting optical power of the optical lens, the plurality of vision accommodation states including at least a failsafe focal distance; and
   a failsafe subsystem including a first sensor coupled to the accommodation actuator to detect a failure condition of the eye-mountable device, wherein the failsafe subsystem includes logic that when executed by the failsafe subsystem causes the eye-mountable device to perform operations including:
      monitoring accommodation values of the accommodation actuator with the first sensor;
      determining the failure condition is detected when the accommodation actuator provides incorrect accommodation values; and
      in response to detecting the failure condition, transitioning the eye-mountable device to a failsafe mode and setting the accommodation actuator to the failsafe focal distance.

2. The device of claim 1, wherein the failsafe focal distance is a far field state.

3. The device of claim 1, further comprising a second sensor coupled to one or more components within the eye-mountable device, and wherein the failsafe subsystem includes further logic that when executed by the failsafe subsystem causes the eye-mountable device to perform further operations including:
   monitoring electrical signal or power usage of the one or more components within the eye-mountable device with the second sensor; and
   determining the failure condition is detected in response to the electrical signal or the power usage of at least one of the one or more components being outside a good range.

4. The device of claim 1, further comprising:
   an antenna coupled to the failsafe subsystem to receive a failsafe command; and wherein the failsafe subsystem includes further logic that when executed by the failsafe subsystem causes the eye-mountable device to perform further operations including:
   in response to receiving the failsafe command, determining the failure condition is detected.

5. The device of claim 1, wherein a default state for the optical power of the optical lens when the eye-mountable device is without power is the failsafe focal distance, and wherein the optical lens reverts to the failsafe focal distance upon a loss of the power to the eye-mountable device.

6. The device of claim 1, wherein the failsafe subsystem includes further logic that when executed by the failsafe subsystem causes the eye-mountable device to perform further operations including:
   monitoring transient electrical properties of the accommodation actuator with the accommodation actuator operation sensor; and
   determining whether a degradation of the accommodation actuator is detected based, at least in part, on the transient electrical properties, and wherein a detection of the degradation indicates the failure condition is detected.

7. An eye-mountable device, comprising:
   an optical lens;
   an accommodation actuator configurable to provide a plurality of vision accommodation states for vision accommodation by adjusting optical power of the optical lens, the plurality of vision accommodation states including at least a failsafe focal distance; and
   a failsafe subsystem including a first sensor coupled to one or more components within the eye-mountable device to detect a failure condition of the eye-mountable device, and wherein the failsafe subsystem includes logic that when executed by the failsafe subsystem causes the eye-mountable device to perform operations including:
      monitoring values of the first sensor to determine whether a timeout condition of the one or more components has occurred, wherein an occurrence of the timeout condition corresponds to detecting the failure condition; and in response to detecting the failure condition, transitioning the eye-mountable device to a failsafe mode and setting the accommodation actuator to the failsafe focal distance.

8. The device of claim 7, wherein the first sensor is an input sensor adapted to receive an input command, and
   wherein the failsafe subsystem includes further logic that when executed by the failsafe subsystem causes the eye-mountable device to perform further operations including:
      overriding an accommodation mode of the eye-mountable device and transitioning the eye-mountable device to the failsafe mode when the input command is received from the input sensor.

9. The device of claim 8, wherein the first sensor is a contact sensor to measure a pressure or strain on the eye-mountable device when the contact sensor is engaged, and wherein an engagement of the first sensor is indicative of the input command.

10. The device of claim 7, further comprising:
    a battery or a capacitor coupled to the accommodation actuator to power the accommodation actuator, and wherein the first sensor is coupled to the battery or the capacitor to measure a voltage or current of the battery or the capacitor, and wherein the failure condition is detected when the voltage or current is outside of a good range.

11. The device of claim 7, wherein the failsafe subsystem includes further logic that when executed by the failsafe subsystem causes the eye-mountable device to perform further operations including:

monitoring a supply voltage value of the one or more components with the first sensor; and determining whether a brownout of the one or more components has occurred in response to the supply voltage falling below a first threshold, and wherein an occurrence of the brownout is indicative of the failure condition being detected.

12. An eye-mountable device, comprising:

an optical lens;

an accommodation actuator configurable to provide a plurality of vision accommodation states for vision accommodation by adjusting optical power of the optical lens, the plurality of vision accommodation states including at least a failsafe focal distance; and a failsafe subsystem including logic that when executed by the failsafe subsystem causes the eye-mountable device to perform operations including:

identifying an initialization or reset of the eye-mountable device; and setting the accommodation actuator of the eye-mountable device to the failsafe focal distance when the initialization or the reset of the eye-mountable device is identified.

13. The device of claim 12, wherein the failsafe subsystem includes further logic that when executed by the failsafe subsystem causes the eye-mountable device to perform further operations including:

locking the accommodation actuator of the eye-mountable device to the failsafe focal distance when the initialization or the reset of the eye-mountable device is identified;

performing a health check of the eye-mountable device upon the reset or the initialization of the eye-mountable device; and unlocking the accommodation actuator of the eye-mountable device upon completion of the health check.

\* \* \* \* \*